United States Patent
Galer et al.

(10) Patent No.: US 9,597,105 B2
(45) Date of Patent: Mar. 21, 2017

(54) VIBRATING SURGICAL INSTRUMENTS FOR BLUNT DISSECTION

(71) Applicant: Covidien LP, Mansfield, MA (US)

(72) Inventors: Katelyn Galer, Austin, TX (US); Justin Williams, Southbury, CT (US); Danyel Racenet, Killingworth, CT (US); Kevin Sniffin, Danbury, CT (US); Stanislaw Marczyk, Stratford, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 285 days.

(21) Appl. No.: 14/551,481

(22) Filed: Nov. 24, 2014

(65) Prior Publication Data

US 2015/0297257 A1     Oct. 22, 2015

Related U.S. Application Data

(60) Provisional application No. 61/980,637, filed on Apr. 17, 2014.

(51) Int. Cl.
  *A61B 17/32* (2006.01)
  *A61B 17/3205* (2006.01)
  *A61B 17/22* (2006.01)
  *A61B 17/00* (2006.01)

(52) U.S. Cl.
  CPC .......... *A61B 17/320068* (2013.01); *A61B 17/32056* (2013.01); *A61B 17/22004* (2013.01);
  (Continued)

(58) Field of Classification Search
  CPC ...... A61B 17/320068; A61B 17/32056; A61B 17/22004; A61B 17/32002;
  (Continued)

(56) References Cited

U.S. PATENT DOCUMENTS

| 6,383,194 | B1 | 5/2002 | Pothula |
| 6,863,677 | B2 | 3/2005 | Breznock |

(Continued)

FOREIGN PATENT DOCUMENTS

EP    1864622 A2    12/2007

OTHER PUBLICATIONS

U.S. Appl. No. 14/551,392, filed Nov. 24, 2014, inventor Katelyn Galer.

(Continued)

*Primary Examiner* — Eric Rosen
*Assistant Examiner* — George J Ulsh

(57) ABSTRACT

A dissector including a body, a first arm, a second arm, and a string. The first arm extending from the body towards a distal end thereof and the second arm extending from the body towards a distal end thereof. One end of the string is coupled to the first arm adjacent the distal end thereof and the other end of the string is coupled to the second arm adjacent the distal end thereof. The first and second arms have an expanded configuration such that the string is taut and have a collapsed configuration such that the string is slack. The string is configured to dissect tissue when the first and second arms are in the expanded configuration. The string may oscillate to dissect tissue. The distal ends of the first and second arms may atraumatically dissect tissue.

18 Claims, 5 Drawing Sheets

(52) U.S. Cl.
CPC ............... *A61B 17/32002* (2013.01); *A61B 2017/00415* (2013.01); *A61B 2017/00876* (2013.01); *A61B 2017/32006* (2013.01); *A61B 2017/320044* (2013.01); *A61B 2017/320076* (2013.01)

(58) Field of Classification Search
CPC  A61B 2017/00415; A61B 2017/00876; A61B 2017/320044; A61B 2017/320076; A61B 17/32; A61B 2017/32006; A61B 10/06; A61B 17/28; A61B 17/30; A61B 17/1606; A61B 17/22031; A61B 17/29; A61B 2017/2936; A61C 15/046; A61C 15/047; A61C 15/048; A61C 17/3481; A61C 17/34; A61C 17/32; A46B 13/02; A46B 13/023; A46B 15/0071; A46B 15/0073
USPC .......................................... 606/169, 205–207
See application file for complete search history.

(56) References Cited

U.S. PATENT DOCUMENTS

| | | |
|---|---|---|
| 7,497,866 B2 | 3/2009 | Perez |
| 7,534,242 B2 | 5/2009 | Buehlmann et al. |
| 7,833,233 B2 | 11/2010 | Mueller et al. |
| 8,002,788 B2 | 8/2011 | Heinrich et al. |
| 8,460,316 B2 | 6/2013 | Wilson et al. |
| 2005/0250986 A1 | 11/2005 | Rothe et al. |
| 2006/0064113 A1* | 3/2006 | Nakao ............. A61B 10/06 606/113 |
| 2006/0173481 A1 | 8/2006 | Thorson |
| 2007/0265649 A1 | 11/2007 | Perez |
| 2007/0282328 A1* | 12/2007 | Yahagi ............ A61B 18/1402 606/45 |
| 2008/0125803 A1 | 5/2008 | Sadamasa et al. |
| 2010/0116287 A1* | 5/2010 | Cohen ............. A61C 15/042 132/323 |
| 2010/0198248 A1 | 8/2010 | Vakharia |
| 2012/0109184 A1 | 5/2012 | Spivey et al. |
| 2012/0296332 A1 | 11/2012 | Chernov et al. |
| 2013/0018402 A1 | 1/2013 | Polo |
| 2013/0317515 A1 | 11/2013 | Kuroda et al. |

OTHER PUBLICATIONS

European Search Report dated Jul. 29, 2015, issued in European Application No. 14199666.

* cited by examiner

VIBRATING SURGICAL INSTRUMENTS FOR BLUNT DISSECTION

CROSS-REFERENCE TO RELATED APPLICATIONS

This application claims the benefit of and priority to U.S. Provisional Patent Application No. 61/980,637, filed Apr. 17, 2014, the entire disclosure of which is incorporated by reference herein.

BACKGROUND

1. Technical Field

The present disclosure relates to surgical instruments and, more specifically, to vibrating surgical instruments for blunt dissection of tissue.

2. Discussion of Related Art

In many types of surgery, it is necessary to remove or displace tissue in order to perform a procedure. Often, this is to improve a surgeon's vision in an area of interest where more delicate operations need to be performed or may be to remove tissue which is in the way for a procedure as it prevents the surgeon from accessing the area of interest with the tools they need to operate on it. One of the more common types of surgery where removal of tissue is necessary is on surgery related to the bowels where it is often necessary to remove tissue in the form of adhesions to access the bowels.

Depending on the nature of the tissue to be removed and its location, various different types of tools are desirable. The most common type of surgical tool to remove tissue is undoubtedly a sharp device such as a scalpel, blade, saw, or drill. These types of devices are necessary for virtually any type of surgery to be performed as they allow the surgeon to cut through what would otherwise be a seamless body structure. In many situations, however, they are preferably not used as should the cutting instrument slip slightly, a dangerous situation could occur. When a surgeon is working near essential blood vessels, organs, or other sensitive structures, misplacement or deviation of a sharp device can result in potential injury.

One way to avoid this type of injury is to utilize a tool that is suitable for separating two types of matter along an existing seam or connection, but is generally unsuitable for "cutting" into seamless matter. This is often referred to as a blunt dissection instrument. Blunt dissection generally allows tissues to be dissected atraumatically by simply separating the tissue along existing seams or natural planes. That is, the tool separates along natural separations, conjunctions, or faults, without the tool creating a new seam. This type of instrument facilitates in surgical exposure and tissue retraction both because of reducing danger to neighboring tissue and reducing trauma from manmade separation.

While blunt dissection is a useful medical procedure, the tools for blunt dissection are often ill suited for the task. Current tools may not provide sufficient force to separate structures without an existing seam and are generally incapable of generating a new seam or separation on its own.

SUMMARY

In an aspect of the present disclosure, a dissector includes a body, a first arm, a second arm, and a string. The first arm extends from the body to a first distal end and the second arm extends from the body to a second distal end. One end of the string is coupled to the first arm adjacent the first distal end and the other end of the string is coupled to the second arm adjacent the second distal end. The string is taut when the first and second arms are in the expanded configuration and the string is slack when the first and second arms are in a collapsed configuration. The string is configured to dissect tissue when the first and second arms are in the expanded configuration.

In embodiments, the first and second distal ends are configured to atraumatically dissect tissue. The first and second arms may be biased towards the expanded configuration.

In some embodiments, the dissector includes a tube that defines a lumen. The body of the dissector may be slidably disposed within the lumen such that the first and second arms extend from a distal end of the tube in the expanded configuration and are at least partially disposed within the lumen in the collapsed configuration. The tube may engage the first and second arms to transition the first and second arms from the expanded configuration to the collapsed configuration. In the collapsed configuration, the first and second distal ends protrude from a distal end of the tube to atraumatically dissect tissue. The first and second arms may have a transport configuration such that the first and second distal ends are disposed within the lumen proximal to a distal end of the tube.

In certain embodiments, in the collapsed configuration the first and second distal ends may protrude from a distal end of the body to atraumatically dissect tissue. The first and second arms may have a transport configuration such that the first and second distal ends are disposed within the body proximal to a distal end of the body.

In particular embodiments, the first and second arms are coupled together and to the body by a pivot pin. The body may define a slot defined in sidewalls of the body parallel to a longitudinal axis of the body. The pivot pin may be slidably disposed within the slot. The dissector may include a biasing member disposed about the pivot pint that biases the first and second arms towards the expanded configuration. The biasing member may be a torsion spring. In certain embodiments, the dissector includes a retraction member coupled to the pivot pin. The retraction member may be configured to retract the pivot pin towards a proximal end of the slot.

In embodiments, the dissector includes a vibration mechanism that is configured to oscillate the string traverse to or along a longitudinal axis of the body. The dissector may include first and second jaw members coupled together at a pivot pin. The first distal end of the first arm may be disposed within the first jaw member and the second distal end of the second arm may be disposed within the second jaw member. The distal ends of the first and second jaw members may be configured to atraumatically dissect tissue. The first and second jaw member may be configured to limit tissue contacting the string when the first and second arms are in the expanded configuration. Proximal portions of the first and second arms may extend proximally within the body. A vibration mechanism may be disposed within the first jaw member.

In some embodiments, the vibration mechanism includes a magnetic coil and a magnet. The magnet may be disposed on the first arm adjacent the first distal end and the magnetic coil may be positioned adjacent the magnet. The magnetic coil is configured to alternately attract and repel the magnet as energy is applied to the magnetic coil such that the string is oscillated.

In certain embodiments, the vibration mechanism includes a rotary element and an eccentric mass. The rotary element is disposed on the first arm adjacent the first distal end. The eccentric mass is rotatable by the rotary element to induce oscillation of the string.

In particular embodiments, the vibration mechanism includes a piezoelectric actuator associated with the first arm that induces oscillation of the string when energy is applied to the piezoelectric actuator. The piezoelectric actuator may be a stripe actuator disposed along the first arm substantially parallel to a longitudinal axis of the first arm or may be a stack actuator disposed adjacent the first distal end.

In other aspects of this disclosure, a dissector includes a body defining a longitudinal axis, a first shaft extending from the body, a peanut, and a vibration mechanism. The peanut is disposed over and coupled to a distal end of the first shaft and configured to atraumatically dissect tissue. The vibration mechanism is configured to oscillate the peanut in a transverse direction to the longitudinal axis of the body or an axial direction to the longitudinal axis of the body.

In embodiments, the dissector includes a second shaft and a knife. The second shaft is slidably disposed within the first shaft and has a retracted position such that a distal end of the second shaft is adjacent the distal end of the first shaft. The knife is coupled to the distal end of the second shaft and is disposed entirely within the peanut when the second shaft is in the retracted position. The knife is configured for sharp dissection of tissue in contact therewith. The second shaft may have a first exposed position such that the distal end of the second shaft extends from the distal end of the first shaft and the knife is at least partially exposed from a distal end of the peanut. The second shaft may have a second exposed position such that the distal end of the second shaft extends from the distal end of the peanut and the knife is fully exposed from the distal end of the peanut. The first shaft may engage the second shaft such that the vibration mechanism oscillates the knife.

In yet another aspect of the present disclosure, a method for dissecting tissue includes inserting a dissector within a surgical site in a collapsed configuration, dissecting tissue with first and second distal ends, expanding first and second arms of the dissector from a collapsed configuration to an expanded configuration, and dissecting tissue with the string. In the collapsed configuration the string is slack and in the expanded configuration the string is taut. The dissector may be any of the dissectors disclosed herein including a body, a first arm, a second arm, and a string.

In aspects, dissecting tissue with the first and second distal ends includes oscillating at least one of the first and second arms with a vibration mechanism. Dissecting tissue with the string may include oscillating the string with a vibration mechanism.

In some aspects, the method may include collapsing the first and second arms to the collapsed configuration after dissecting tissue. The method may include dissecting tissue with the first and second distal ends of the dissector after collapsing the first and second arms. Collapsing the first and second arms may include retracting a pivot pin within a slot defined in the body to retract portions of the first and second arms into the body.

In certain aspects, expanding the first and second arms includes retraction a tube from over a distal end of the body with the body is disposed within a lumen of the tube. Alternatively, expanding the first and second arms may include extending the body from a distal end of the tube with the body disposed within a lumen of the tube.

In still yet another aspect of the present disclosure, a method for dissecting tissue includes inserting a dissector within a surgical site in a collapsed configuration, dissecting tissue with distal ends of first and second jaw members, opening the first and second jaw members, and dissecting tissue with the string. Opening the first and second jaw members expands first and second arms of the dissector from the collapsed configuration to an expanded configuration. In the collapsed configuration a string coupled to the first and second arms is slack and in the expanded configuration the string is taut between the first and second arms. The dissector may be any of the dissectors disclosed herein including a body, a first arm, a second arm, a string, a first jaw member, and a second jaw member.

In aspects, dissecting tissue with the string includes oscillating the string with a vibration mechanism. In embodiments, oscillating the string may include energizing a magnetic coil disposed within the first jaw member adjacent a magnet disposed on the first arm adjacent the first distal end. In some embodiments, oscillating the string includes energizing a rotary element disposed on the first arm adjacent the first distal end and within the first jaw member. The rotary element rotating an unbalanced mass to induce oscillation in the string. In certain embodiments, oscillating the string includes energizing a piezoelectric actuator associated with the first arm. The method may include dissecting tissue with distal ends of the first and second jaw members after closing the first and second jaw members In particular aspects, the method includes guiding tissue to be dissected with the string towards the string positioned between the first and second jaw members. The first and second jaw members may guide the tissue.

In some aspects, the method includes closing the first and second jaw members collapses the first and second arms to the collapsed configuration after dissecting tissue with the string.

In still another aspect of the present disclosure, a method for dissecting tissue includes inserting a dissector within a surgical site and dissecting tissue with a peanut by oscillating the peanut with a vibration mechanism. The dissector may be any of the dissectors disclosed herein including a body, a first shaft, a peanut, and a vibration mechanism.

In aspects, the method includes extending a knife from within the peanut and dissecting tissue with the knife. The method may include retracting the knife within the peanut after dissecting tissue.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
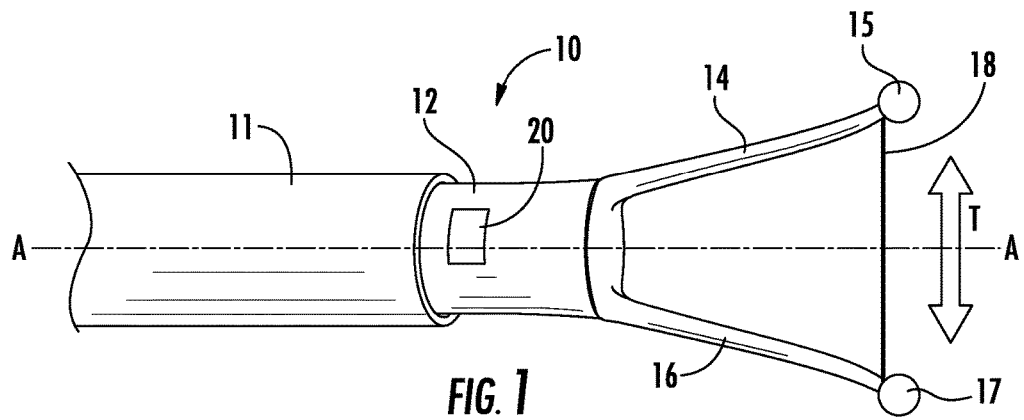
FIG. 1 is a top view of a dissector provided in accordance with the present disclosure in an expanded configuration.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Blunt dissection of tissue is preferred when dissecting tissue near blood vessels or organs that may be damaged when contacted with a sharp instrument. However, some adhesions between bodily structures may not be easily dissected when contacted with a blunt dissector. Additional energy or movement of the dissector may be required to dissect these adhesions. By incorporating features in a dissector that permit a dissector to bluntly dissect tissue and apply additional energy or movement to tissue when required to dissect the tissue may reduce the time of a procedure and thus the cost of the procedure. In addition, such a dissector may increase the safety of a procedure. The additional energy or movement may be vibratory movement as detailed below. Additionally or alternatively, a dissector that may bluntly dissect tissue, transition to sharply dissect tissue when needed, and then transition back to bluntly dissect additional tissue may have the same advantages detailed above.

Referring now to FIG. 1, a dissector 10 is provided in accordance with the present disclosure and includes a body 12, a first arm 14, a second arm 16, and a string 18. The first arm 14 extends from the body 12 to a distal end 15 and the second arm 16 extends from the body 12 to a distal end 17 in substantially the same direction as the first arm 14. The distal ends 15, 17 may be substantially the same distance from the body 12. The distal ends 15, 17 are blunt such that the distal ends 15, 17 may atraumatically dissect tissue. One end of the string 18 is coupled to the first arm 14 adjacent the distal end 15 and the other end of the string 18 is coupled to the second arm 16 adjacent the distal end 17. The distal end 15 of the first arm 14 is biased away from the distal end 17 of the second arm 17 such that the string 18 is taut. The body 12 of the dissector 10 may extend from a lumen of a tube 11.

Figure 2:
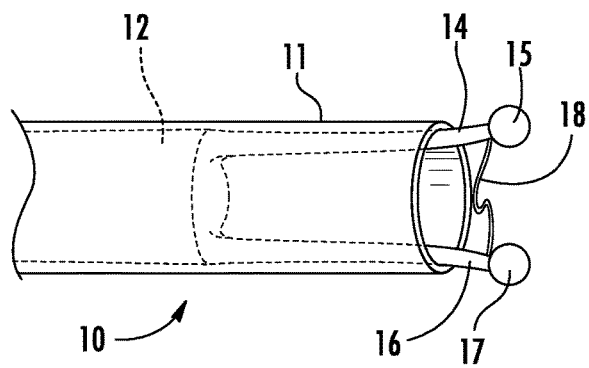
FIG. 2 is a top view of the dissector of FIG. 1 in a collapsed configuration.

With additional reference to FIG. 2, the dissector 10 has an expanded configuration (FIG. 1) and a collapsed configuration (FIG. 2). In the expanded configuration, the first and second arms 14, 16 are positioned distally of a distal end of the tube 11 such that the string 18 is made taut by the distal ends 15, 17 being biased away from one another. In the collapsed configuration, the body 12 is retracted into tube 11 or the tube 11 is extended over the body 12 such that the tube 11 engages the first and second arms 14, 16 to urge the first and second arms 14, 16 and the distal ends 15, 17 towards one another and into the collapsed configuration. In the collapsed configuration the distal ends 15, 17 protrude beyond the distal end of the tube 11 such that the distal ends 15, 17 may be used for blunt dissection of tissue. When the in the collapsed configuration, the string 18 is slack between the first and second arms 14, 16.

Figure 3:
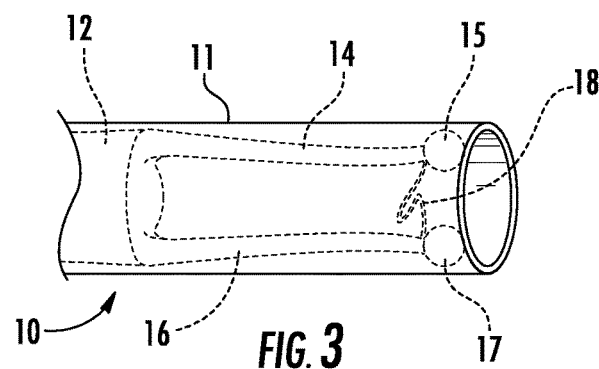
FIG. 3 is a top view of the dissector of FIG. 1 in a transport configuration.

Referring to FIG. 3, the dissector 10 may include a transport configuration such that the distal ends 15, 17 are disposed within the tube 11. In the transport configuration, the string 18 may be disposed within the tube 11 or outside of the tube 11. In certain embodiments, the tube 11 may be a catheter tube positioned adjacent to tissue to be dissected and the dissector 10 is delivered through the catheter tube to the tissue to be dissected.

In embodiments, the dissector 10 includes a vibration mechanism 20 configured to laterally vibrate the string 18. The vibration mechanism 20 may be operatively associated with one or more of the tube 11, the body 12, the first arm 14, and the second arm 16.

In use, the dissector 10 is inserted into a surgical site in the collapsed configuration. The surgical site may be an opening (e.g., natural orifice or incision) providing access to a body cavity of a patient. The dissector 10 may be inserted through a cannula or an access port (not shown). When the distal ends 15, 17 are adjacent or in contact with tissue to be dissected, the body 12 or tube 11 of the dissector 10 are manipulated to dissect tissue with the distal ends 15, 17. In some instances, the distal ends 15, 17 of the dissector 10 may not bluntly dissect tissue in contact therewith. In these instances, the dissector 10 may be transitioned to the expanded configuration by extending the body 12 from the tube 11 or retracting the tube 11 from over the arms 14, 16.

When the dissector 10 transitions to the expanded configuration and the string 18 is taut between the distal ends 15, 17 of the first and second arms 14, 16, the string 18 may be used to dissect tissue. With the dissector 10 in the expanded configuration the tube 11 or the body 12 may be laterally vibrated to dissect tissue with the string 18. It will be appreciated that lateral vibration is oscillating movement of the string 18 in a direction transverse to a longitudinal axis A-A of the body 12 in a plane common with the distal ends 15, 17 as represented by the arrows T in FIG. 1. Additionally or alternatively, the vibration mechanism 20 may be configured to vibrate at least one of the first and second arms 14, 16 to vibrate the string 18.

Figure 4:
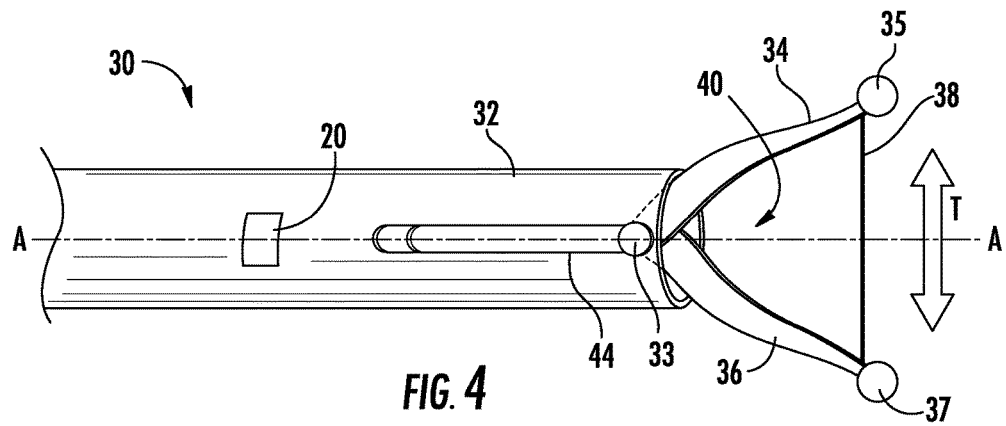
FIG. 4 is a top view of another dissector provided in accordance with the present disclosure in an expanded configuration.
Figure 5:
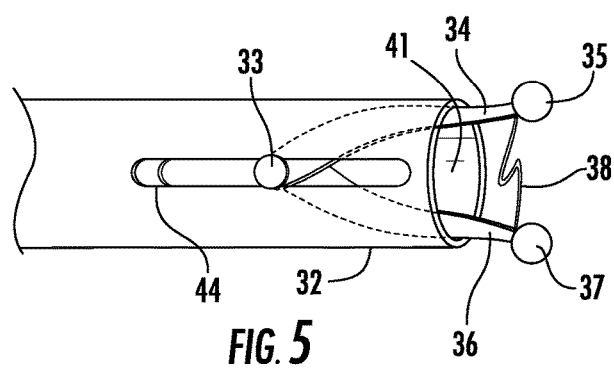
FIG. 5 is a top view of the dissector of FIG. 4 in a collapsed configuration.

With reference to FIGS. 4 and 5, another dissector 30 is provided in accordance with the present disclosure including a body 32, a pivot pin 33, a first arm 34, a second arm 36, and a string 38. The first arm 34 is a rigid member that extends from the body 32 to a distal end 35 and the second arm 36 is a rigid member that extends from the body 32 to a distal end 37 in substantially the same direction as the first arm 34. The distal ends 35, 37 may be substantially the same distance from the body 32. The distal ends 35, 37 are blunt such that the distal ends 35, 37 may atraumatically dissect tissue. One end of the string 38 is coupled to the first arm 34 adjacent the distal end 35 and the other end of the string 38 is coupled to the second arm 36 adjacent the distal end 37.

The pivot pin 33 is adjacent a distal end of the body 32. A proximal end of the first arm 34 and a proximal end of the second arm 36 are coupled to the body 32 by the pivot pin 33. The dissector 30 has an expanded configuration (FIG. 4) and a collapsed configuration (FIG. 5). In the expanded configuration, the distal ends 35, 37 of the first and second arms 34, 36, respectively, are spaced-apart and the string 38 is taut between the first and second arms 34, 36. In the collapsed configuration, the distal ends 35, 37 of the first and second arms 34, 36, respectively, are close to one another such that the string 38 is slack between the first and second arms 34, 36. In the collapsed position, the distal ends 35, 37 may be used for blunt dissection of tissue.

Figure 7:
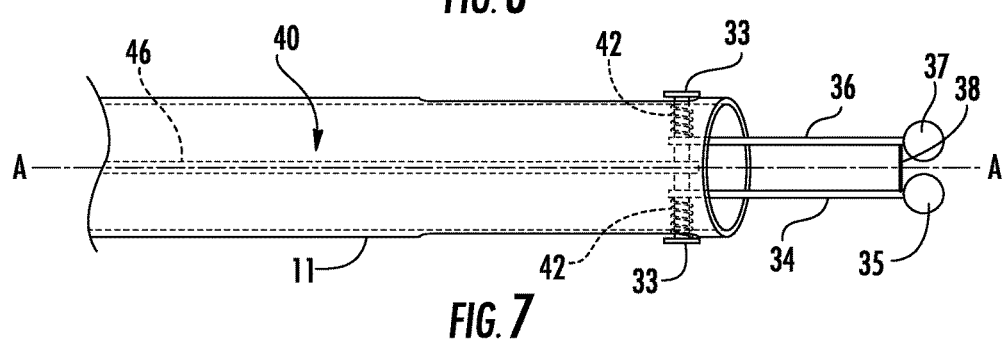
FIG. 7 is a side view of the dissector of FIG. 4.

With additional reference to FIG. 7, the dissector 30 includes an actuation mechanism 40 configured to transition the dissector 30 between the expanded configuration and the collapsed configuration. The actuation mechanism 40 may include a biasing member 42 positioned about pivot pin 33 to bias the dissector 30 towards the expanded configuration. The biasing member 42 may be a torsion spring.

Figure 6:
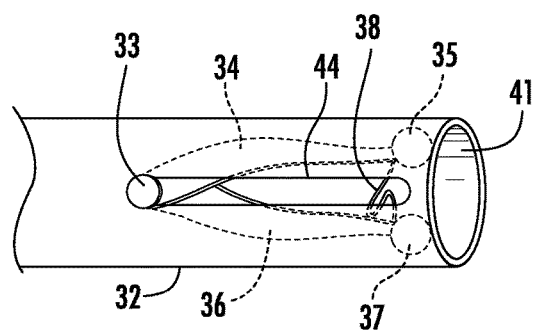
FIG. 6 is a top view of the dissector of FIG. 4 in a transport configuration.

In some embodiments, the body 32 defines a lumen 41 and the pivot pin 33 is disposed within a slot 44 defined in sidewalls of the body 32 substantially parallel to a longitudinal axis A-A of the body 32. In addition, the actuation mechanism 40 includes a retractable member 46 coupled to the pivot pin 33. The retractable member 46 configured to translate the pivot pin 33 within the slot 44 along the longitudinal axis of the body 32 to transition the dissector 30 between the expanded configuration, the collapsed configuration, and the transport configuration. The retractable member 46 may be disposed within the lumen 41 of the body 30. For example, when the pivot pin 33 is positioned adjacent a distal end of the slot 44 the dissector 30 is in the expanded configuration and when the pivot pin 33 is positioned adjacent a proximal end of the slot 44, the body 32 of the dissector 30 engages the arms 34, 36 to collapse the dissector 30 to the collapsed configuration. When in the collapsed configuration, the distal ends 35, 37 may protrude from the distal end of the body 32. In certain embodiments, the retractable member 44 may translate the pivot pin 33 until the distal ends 35, 37 are drawn into the body 32 of the dissector 30 such that the dissector 30 is in a transport configuration as shown in FIG. 6. The first and second arms 34, 36, being biased by the biasing member 42, may bias the dissector 30 to the expanded configuration. Additionally or alternatively, the actuation mechanism 40 includes a tube (not shown) substantially similar to the tube 11 of the dissector 10 detailed above, as such the tube and the use thereof will not be described in detail for reasons of brevity.

The dissector 30 may be used substantially similar to the dissector 10 detailed above, as such the use of dissector 30 will not be detailed for reasons of brevity. In embodiments, the dissector 30 includes the vibration mechanism 20 configured to laterally vibrate the string 38. The vibration mechanism 20 may be operatively associated with one or more of the body 32, the first arm 34, and the second arm 36.

Figure 8:
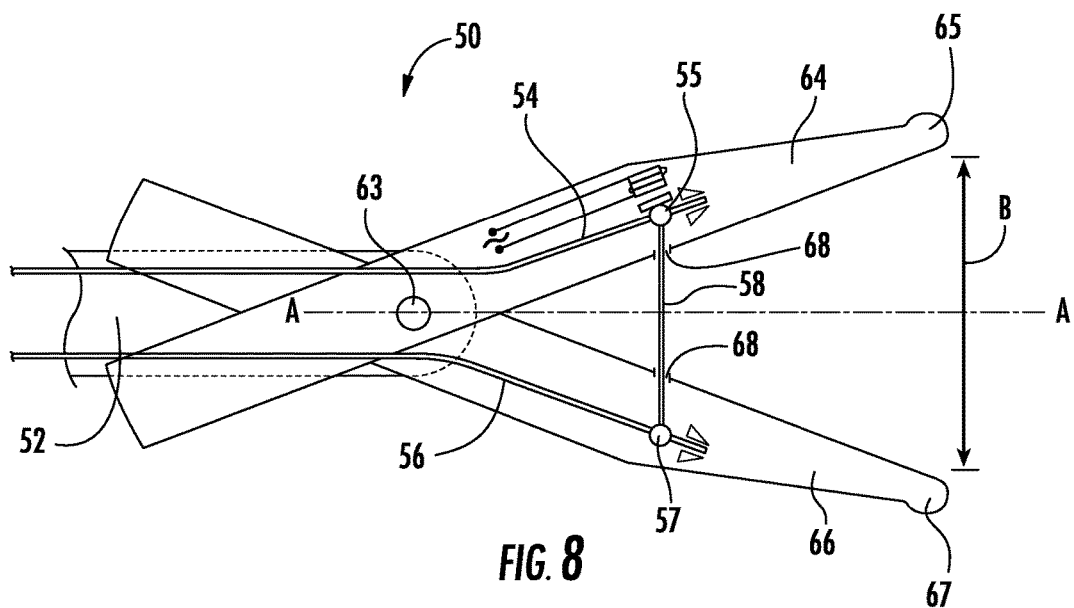
FIG. 8 is a side cut-away view of yet another dissector provided in accordance with the present disclosure with a jaw members in an open condition and the dissector in an expanded configuration.
Figure 9:
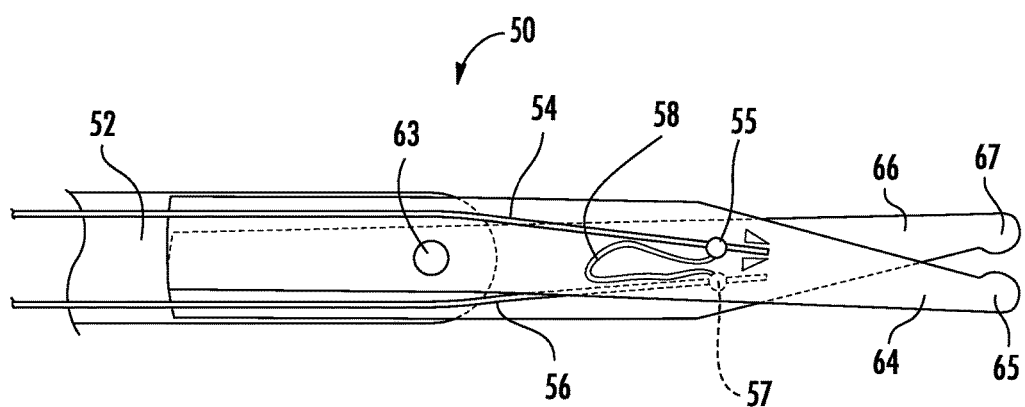
FIG. 9 is a side cut-away view of the dissector of FIG. 8 with the jaw members in a closed condition and the dissector in a collapsed configuration.

With reference to FIGS. 8 and 9, yet another dissector 50 is provided in accordance with the present disclosure and includes a body 52, a first arm 54, a second arm 56, a string 58, a first jaw member 64, and a second jaw member 66. The first jaw member 64 extends from the body 52 to a distal end 65 and the second jaw member 66 extends from the body 52 to a distal end 67. The distal ends 65, 67 are blunt to atraumatically contact and dissect tissue in contact therewith. The first and second jaw members 64, 66 are coupled by a pivot pin or pivot 63 adjacent a distal end of the body 52. The first and second jaw members 64, 66 may be moveable relative to one another between an open condition (FIG. 8) and a closed condition (FIG. 9). In the open condition, the distal ends 65, 67 are spaced-apart a distance B as detailed below.

The first arm 54 is at least partially disposed within the first jaw member 64 and the second arm 56 is at least partially disposed within the second jaw member 66. It is also within the scope of this disclosure that the first and second arms 54, 56 may be disposed on the outer surface of the first and second jaw members 64, 66 respectively. Proximal ends of each of the first and second arms 54, 56 extend proximally within the body 52. Alternatively, the proximal ends of each of the first and second arms 54, 56 may be fixed within and relative to a respective one of the first and second jaw members 64, 66 adjacent the distal end of the body 52. A distal end 55 of the first arm 54 is disposed within the first jaw member 64 and a distal end 57 of the second arm 56 is disposed within the second jaw member 66. The distal ends 55, 57 are substantially free to move transverse to a longitudinal axis A-A of the body and may be substantially free to move along the longitudinal axis A-A of a respective one of the jaw members 64, 66. The distal ends 55, 57 may be positioned about halfway along a length of a respective one of the first and second jaw members 64, 66 from the pivot 63 to a respective one of the distal ends 65, 67. The first and second arms 54, 56 are flexible such that each of the first and second arms 54, 56 functions as a leaf spring with the proximal ends thereof fixed and the distal ends 55, 57 thereof substantially free.

The surfaces of the first and second jaw members 64, 66 opposing one another each define an opening 68. The string 58 passes through the openings 68 with one end of the string 58 coupled to the first arm 54 adjacent the distal end 55 and the other end of the string 58 coupled to the second arm 56 adjacent the distal end 57. When the first and second jaw members 64, 66 are in the open condition as shown in FIG. 8, the first and second arms 54, 56 are in an expanded configuration such that the string 58 is taut and when the first and second jaw members 64, 66 are in the closed condition as shown in FIG. 9, the first and second arms 54, 56 are in a collapsed configuration such that the string 58 is slack.

Figure 10:
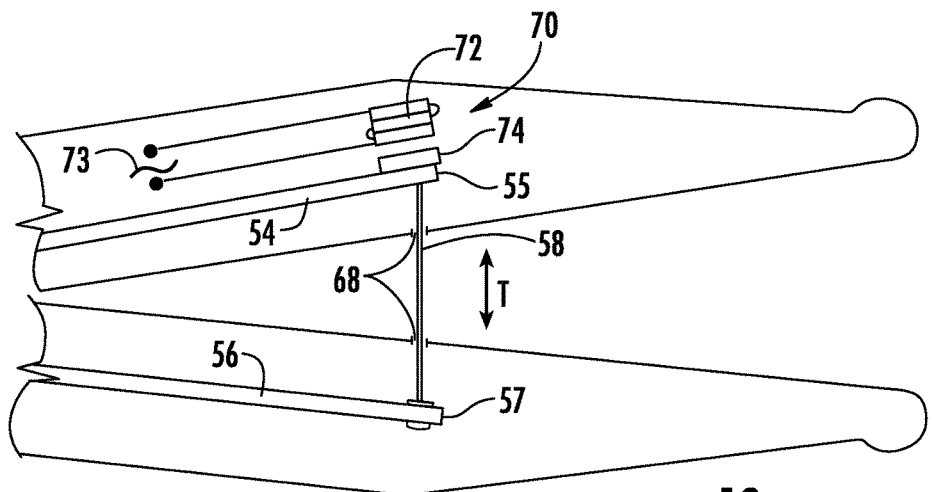
FIG. 10 is an enlarged side cut-away view of a vibration mechanism disposed within the jaw members of the dissector of FIG. 8.
Figure 11:
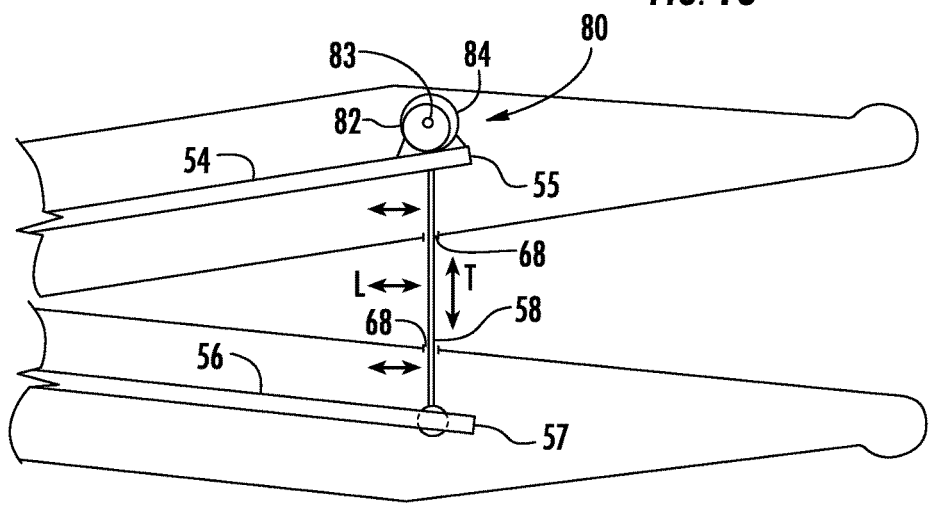
FIG. 11 is an enlarged side cut-away view of a another vibration mechanism disposed within the jaw members of the dissector of FIG. 8 in accordance with the present disclosure.
Figure 12:
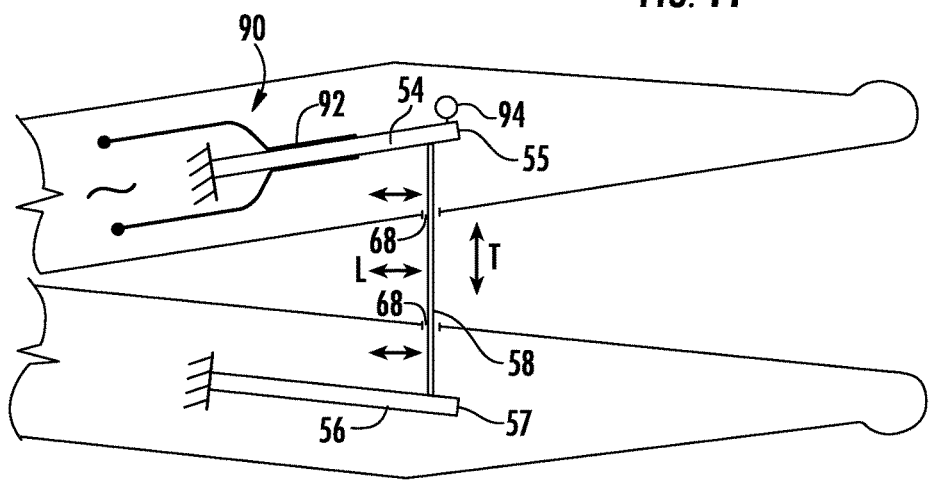
FIG. 12 is an enlarged side cut-away view of a yet another vibration mechanism disposed within the jaw members of the dissector of FIG. 8 in accordance with the present disclosure.

With reference to FIGS. 10-12, exemplary embodiments of vibration mechanisms 70, 80, 90 may be associated with the dissector 50 to induce oscillation (e.g., lateral, represented by arrows T, or longitudinal, represented by the arrows L, oscillation) of the string 58 when the string 58 is taut. The jaw members 64, 66 are substantially isolated from the vibration mechanism 70, 80, 90 such that the jaw members 64, 66 remain substantially stationary during the oscillation of the string 58.

Referring now to FIG. 10, a vibration mechanism 70 includes a magnetic coil 72 and a magnet 74. The magnet 74 is coupled to the first arm 54 adjacent the distal end 55. In embodiments, the magnet 74 is integrally formed with the first arm 54. The magnetic coil 72 is disposed within the first jaw member 64 adjacent the magnet 74. The magnetic coil 72 is in communication with an energy source 73 that induces a magnetic field about the magnetic coil 72. The magnetic field about the magnetic coil 72 alternates to attract and repel the magnet 74 to induce oscillation of the string 58

(e.g., lateral oscillation). The energy source 73 may be disposed within the dissector 50 or be external to the dissector 50. The vibration mechanism 70 may induce vibration in one of the first and second arms 54, 56 substantially similar to the resonant frequency of the one of the first and second arms 54, 56.

With reference to FIG. 11, a vibration mechanism 80 includes a rotary element 82 disposed on the first arm 54. The rotary element 82 may be positioned adjacent the distal end 55 of the first arm 54. The rotary element 82 includes an eccentric mass 84 configured to rotate about a center point 83 of the rotary element 82. The rotary element 82 may be a rotary motor. The rotation of the eccentric mass 84 about the center point 83 induces oscillation of the string 58. It will be appreciated that depending on the orientation of the rotary element 82, the oscillation of the string 58 may be lateral or longitudinal. For example, as shown in FIG. 11, the eccentric mass 84 rotates substantially parallel to the longitudinal axis of the first arm 54 inducing lateral oscillation of the string 58 (i.e., oscillation transverse to the longitudinal axis as represented by arrows T in FIG. 11). Alternatively, the eccentric mass 84 may rotate orthogonal to the longitudinal axis of the first arm 54 inducing longitudinal oscillation of the string 58 (i.e., oscillation along the longitudinal axis as represented by arrows L in FIG. 11). The vibration mechanism 80 may induce vibration in one of the first and second arms 54, 56 substantially similar to the resonant frequency of the one of the first and second arms 54, 56.

Referring to FIG. 12, a vibration mechanism 90 includes one or more piezoelectric actuators 92, 94 associated with the first arm 54. The piezoelectric actuator 92 is a stripe actuator disposed on an outer surface of the first arm 54 such that when an electrical input is applied to the actuator 92, the actuator 92 deflects the first arm 54 to induce oscillation of the string 58. It will be appreciated that depending on the position of the actuator 92 along the first arm 54, the oscillation of the string 58 may be lateral or longitudinal. For example, as shown in FIG. 12, the actuator 92 is positioned along a top surface of the first arm 54 to induce vibration in the first arm 54 towards and away from second arm 56 to induce lateral oscillation of the string 58 (i.e., oscillation transverse to the longitudinal axis as represented by arrows T in FIG. 12). Additionally or alternatively, the actuator 92 may be positioned along a side surface of the first arm 54 (i.e., rotated 90°) to induce longitudinal oscillation of the string 58 (i.e., oscillation along the longitudinal axis as represented by arrows L in FIG. 12).

The piezoelectric actuator 94 is a stack actuator coupled to the first arm 54 adjacent the distal end 55 such that when an electrical input is applied to the actuator 94, the actuator 94 deflects the first arm 54 to induce oscillation of the string 58. It will be appreciated that depending on the position of the actuator 94, the oscillation of the string 58 may be lateral or longitudinal. For example, as shown in FIG. 12, the actuator 94 is positioned substantially orthogonal to the longitudinal axis of the first jaw member 64 to induce lateral oscillation of the string 58 (i.e., oscillation transverse to the longitudinal axis as represented by arrows T in FIG. 12). Alternatively, the actuator 94 may be positioned substantially inline with the longitudinal axis of the first jaw member 64 to induce longitudinal oscillation of the string 58 (i.e., oscillation along the longitudinal axis as represented by arrows L in FIG. 12).

The vibration mechanism 90 may induce vibration in one of the first and second arms 54, 56 substantially similar to the resonant frequency of the one of the first and second arms 54, 56. It is within the scope of this disclosure that a vibration mechanism 90 may include an actuator 92 and an actuator 94.

As shown, each of the vibration mechanisms 70, 80, 90 are disposed within the first jaw member to act directly on the first arm 54; however, it is within the scope of this disclosure that any of the vibration mechanisms 70, 80, 90 may also be disposed within the second jaw member 66 to act directly on the second arm 56. In addition, it is contemplated that one or more of the vibration mechanisms 70, 80, 90 may be disposed within the first jaw member 64 or the second jaw member 66. The vibration mechanism vibrates the device in the sonic range (10-20K Hz).

In use, the dissector 50 is inserted into a surgical site with the jaw members 64, 66 in the closed condition. The distal ends 65, 67 of the jaw members 64, 66 may be used to dissect tissue. In some instances, the distal ends 65, 67 may not bluntly dissect tissue in contact therewith. In these instances, the jaw members 64, 66 may be transitioned to the open configuration. In the open configuration as shown in FIG. 8, the first and second jaw members 64, 66 are spaced apart a distance B. The distance B may allow target tissue (i.e., tissue to be dissected) to pass between the first and second jaw members 64, 66 and prevent non-targeted tissue from passing between the first and second jaw members 64, 66. For example, adhesions may be permitted to pass between the first and second jaw members 64, 66 and bowels may be prevented from passing between the first and second jaw members 64, 66.

When the first and second jaw members 64, 66 are in the open condition, the first and second jaw members 64, 66 are advanced to guide the targeted tissue towards the string 58. It will be appreciated that when the first and second jaw members 64, 66 are in the open condition, the dissector 50 is in the expanded configuration such that the string 58 is taut. The string 58 is then oscillated either manually or with one or more of the vibration mechanisms 70, 80, 90 detailed above to dissect the targeted tissue.

Figure 13:
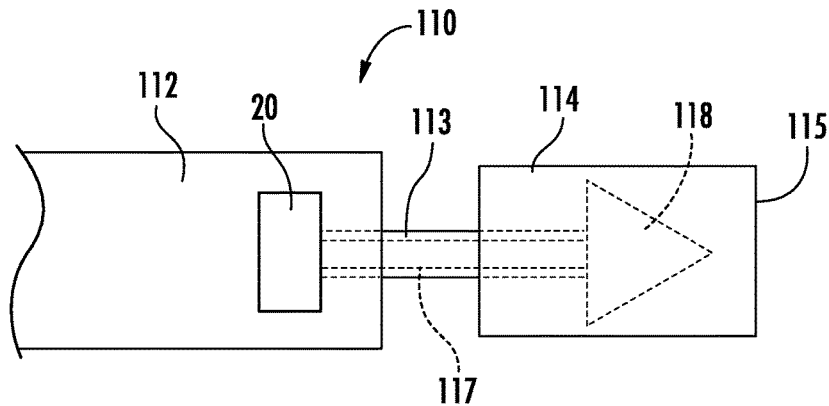
FIG. 13 is a side view of still yet another dissector provided in accordance with the present disclosure with a retractable knife in a retracted position.
Figure 14:
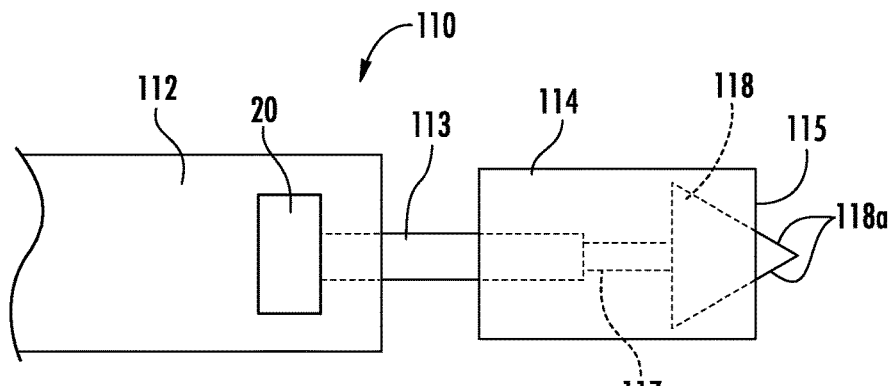
FIG. 14 is a side view of the dissector of FIG. 12 with the retractable knife in a first exposed position and FIG. 15 is a side view of the dissector of FIG. 12 with the retractable knife in a second exposed position.
Figure 15:
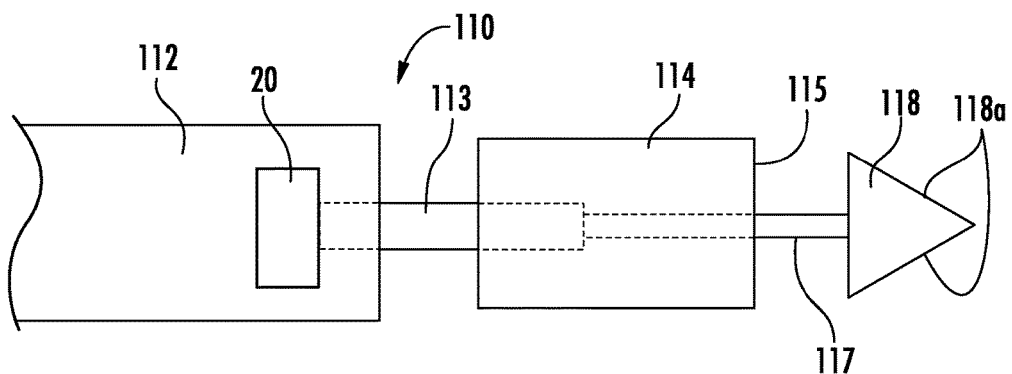

Referring now to FIGS. 13-15, still yet another dissector 110 is provided in accordance with the present disclosure and includes a body 112, a peanut 114, and a retractable knife 118. The peanut 114 is attached to a peanut shaft 113 that extends from a distal end of the body 112. The peanut 114 has a blunt distal end portion 115 for atraumatically dissecting tissue in contact therewith. The peanut 114 may be made of an absorbent material such that the peanut 114 may absorb fluids that result from the dissection of tissue (e.g., blood). The peanut shaft 113 may be operatively associated with the vibration mechanism 20 to induce lateral and/or longitudinal vibration of the peanut 114. The vibration of the peanut 114 may assist in the dissection of tissue in contact with the peanut 114.

The retractable knife 118 has a retracted position (FIG. 13), a first exposed position (FIG. 14), and a second exposed position (FIG. 15). In the retracted position, the retractable knife 118 is disposed within the peanut 114 such that the sharp edges of the retractable knife 118 are prevented from contacting tissue. In the first exposed position, the retractable knife 118 partially extends from the distal end portion 115 of the peanut 114 such that leading edges 118*a* of the retractable knife are at least partially exposed to cut tissue in contact therewith. In the second exposed position, the retractable knife 118 extends from the distal end portion 115 of the peanut 114. The leading edges 118*a* of the retractable knife 118 are sharpened to cut tissue in contact therewith. The retractable knife 118 may be coupled to the distal end of a knife shaft 117. The knife shaft 117 may extend from the proximal end of the retractable knife 118, through the peanut shaft 113, and into the body 112. The knife 118 may vibrate with the peanut 114 when in the retracted position or the exposed position.

In use, the dissector 110 is inserted into a surgical site with the retractable knife 118 in the retracted position. Similar to dissector 10 described above, the dissector 110 may be inserted through an access port (not shown). When the distal end portion 115 of the peanut 114 is adjacent or in contact with tissue to be dissected, the body 112 is manipulated such that the distal end portion 115 atraumatically dissects tissue. When additional dissection is needed, the vibration mechanism 20 may be activated to induce vibration in the peanut 114. The vibration of the peanut 114 may assist the distal end portion 115 in atraumatically dissecting tissue. If the vibration of the peanut 114 still does not permit the distal end portion 115 to dissect the tissue, the retractable knife blade 118 may be exposed from within the peanut 114 such that the leading edges 118a sharply dissect the tissue. The retractable knife blade 118 may then be returned to the retracted position such that the peanut 114 may be used to bluntly dissect additional tissue.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A dissector comprising: a body; a first arm extending from the body to a first distal end thereof; a second arm extending from the body to a second distal end thereof; and a string with one end coupled to the first arm adjacent the first distal end and the other end coupled to the second arm adjacent the second distal end, the string being taut when the first and second arms are in an expanded configuration and the string being slack when the first and second arms are in a collapsed configuration, the string configured to dissect tissue when the first and second arms are in the expanded configuration; the dissector further comprising a vibration mechanism configured to oscillate the string at least one of traverse to a longitudinal axis of the body and along the longitudinal axis of the body, and wherein the vibration mechanism is disposed on the first arm.

2. The dissector of claim 1, wherein the first distal end of the first arm and the second distal end of the second arm are configured to atraumatically dissect tissue.

3. The dissector of claim 2, wherein the first and second arms have a transport configuration such that the first and second distal ends are disposed within the body proximal to a distal end of the body.

4. The dissector of claim 1, wherein the first and second arms are biased towards the expanded configuration.

5. The dissector of claim 1 further comprising a tube defining a lumen, the body slidably disposed within the lumen such that the first and second arms extend from a distal end of the tube in the expanded configuration and are at least partially disposed within the lumen when the first and second arms are in the collapsed configuration and the tube engages the first and second arms to transition the first and second arms from the expanded configuration to the collapsed configuration.

6. The dissector of claim 1, wherein the first and second arms are coupled together and to the body by a pivot pin.

7. The dissector of claim 6, wherein the body defines a slot defined in sidewalls thereof parallel to a longitudinal axis thereof, the pivot pin slidably disposed within the slot.

8. The dissector of claim 7, wherein in the expanded configuration the pivot pin is adjacent a distal end of the slot and in the collapsed configuration the pivot pin is adjacent a proximal end of the slot.

9. The dissector of claim 8 further comprising a biasing member disposed about the pivot pin to bias the first and second arms towards the expanded configuration.

10. The dissector of claim 9, wherein the biasing member is a torsion spring.

11. The dissector of claim 8 further comprising a retraction member coupled to the pivot pin, the retraction member configured to retract the pivot pin towards a proximal end of the slot.

12. The dissector of claim 1, wherein the vibration mechanism vibrates at a frequency of from ten Hertz to twenty thousand Hertz.

13. The dissector of claim 12, wherein the vibration mechanism includes a magnetic coil and a magnet, the magnet disposed on the first arm adjacent the first distal end and the magnetic coil is positioned adjacent the magnet, the magnetic coil configured to alternately attract and repel the magnet as energy is applied to the magnetic coil to oscillate the string.

14. The dissector of claim 12, wherein the vibration mechanism includes a rotary element and an eccentric mass, the rotary element disposed on the first arm adjacent the first distal end, the eccentric mass rotatable by the rotary element to induce oscillation of the string.

15. The dissector of claim 12, wherein the vibration mechanism includes a piezoelectric actuator associated with the first arm to induce oscillation of the string when energy is applied to the piezoelectric actuator.

16. The dissector of claim 15, wherein the piezoelectric actuator is a stripe actuator disposed along the first arm substantially parallel to a longitudinal axis of the first arm.

17. The dissector of claim 15, wherein the piezoelectric actuator is a stack actuator disposed adjacent the first distal end.

18. The dissector of claim 1 further comprising a first jaw member and a second jaw member coupled together at a pivot pin, the first distal end of the first arm is disposed within the first jaw member and the second distal end of the second arm is disposed within the second jaw member.

* * * * *